United States Patent
Peltz et al.

(10) Patent No.: US 9,175,356 B2
(45) Date of Patent: Nov. 3, 2015

(54) INFECTIOUS DISEASE DETECTION SYSTEM

(71) Applicant: The Boeing Company, Chicago, IL (US)

(72) Inventors: Leora Peltz, Pasadena, CA (US); Shawn Hyunsoo Park, Cerritos, CA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/591,647

(22) Filed: Jan. 7, 2015

(65) Prior Publication Data

US 2015/0125937 A1 May 7, 2015

Related U.S. Application Data

(62) Division of application No. 13/302,245, filed on Nov. 22, 2011, now Pat. No. 8,936,944.

(51) Int. Cl.
| | |
|---|---|
| C12Q 3/00 | (2006.01) |
| G01N 15/02 | (2006.01) |
| G06F 19/00 | (2011.01) |
| C12M 1/36 | (2006.01) |

(52) U.S. Cl.
CPC ............... C12Q 3/00 (2013.01); C12M 41/48 (2013.01); G01N 15/0255 (2013.01); G06F 19/3493 (2013.01)

(58) Field of Classification Search
CPC ...... G08B 21/12; G08B 31/00; G08B 15/004; G01N 2001/2223; G01N 1/2202; H01L 2924/0002; A61B 2560/0242
See application file for complete search history.

(56) References Cited

U.S. PATENT DOCUMENTS

| | | | |
|---|---|---|---|
| 6,608,559 B1 * | 8/2003 | Lemelson et al. | 340/539.13 |
| 7,034,677 B2 * | 4/2006 | Steinthal et al. | 340/539.12 |
| 7,591,980 B2 * | 9/2009 | Call et al. | 422/91 |
| 7,864,039 B2 | 1/2011 | Georgeson | |
| 2004/0166550 A1 | 8/2004 | Sullivan et al. | |
| 2004/0262298 A1 | 12/2004 | Thompson et al. | |
| 2006/0274918 A1 * | 12/2006 | Amantea et al. | 382/117 |
| 2007/0053188 A1 | 3/2007 | New et al. | |
| 2008/0163670 A1 | 7/2008 | Georgeson | |
| 2009/0242799 A1 * | 10/2009 | Bolotin et al. | 250/459.1 |
| 2010/0253509 A1 * | 10/2010 | Fu et al. | 340/539.22 |
| 2013/0130227 A1 | 5/2013 | Peltz et al. | |

OTHER PUBLICATIONS

PCT search report dated Feb. 14, 2013 regarding application PCT/US2012/053687, filing date Sep. 4, 2012, applicant The Boeing Company, 10 pages.

"Project Title: Disease Transmission on Aircraft," ACER Airliner Cabin Environment Research, ACER Center of Excellence, 2011, 2 pps., accessed Nov. 18, 2011, http://acer-coe.org/research/disease-transmission.html.

(Continued)

*Primary Examiner* — Sally Merkling
(74) *Attorney, Agent, or Firm* — Yee & Associates, P.C.

(57) ABSTRACT

A method and apparatus for managing a zone. Information is obtained about an environment in the zone with a sensor system. A determination is made by an analyzer system as to whether a contagious condition is present in the zone using the information from the sensor system. An action is performed by a management system in response to the contagious condition being present.

18 Claims, 6 Drawing Sheets

(56) References Cited

OTHER PUBLICATIONS

Mangili et al., "Transmission of infectious diseases during commercial air travel," Elsevier, Inc., The Lancet, vol. 365, Issue. 9463, Mar. 2005, pp. 989-996.

Office action dated May 6, 2013 regarding U.S. Appl. No. 13/302,245, 13 pages.
Final Office action dated Sep. 9, 2013 regarding U.S. Appl. No. 13/302,245, 11 pages.
Notice of Allowance dated Sep. 12, 2014 regarding U.S. Appl. No. 13/302,245, 9 pages.

* cited by examiner

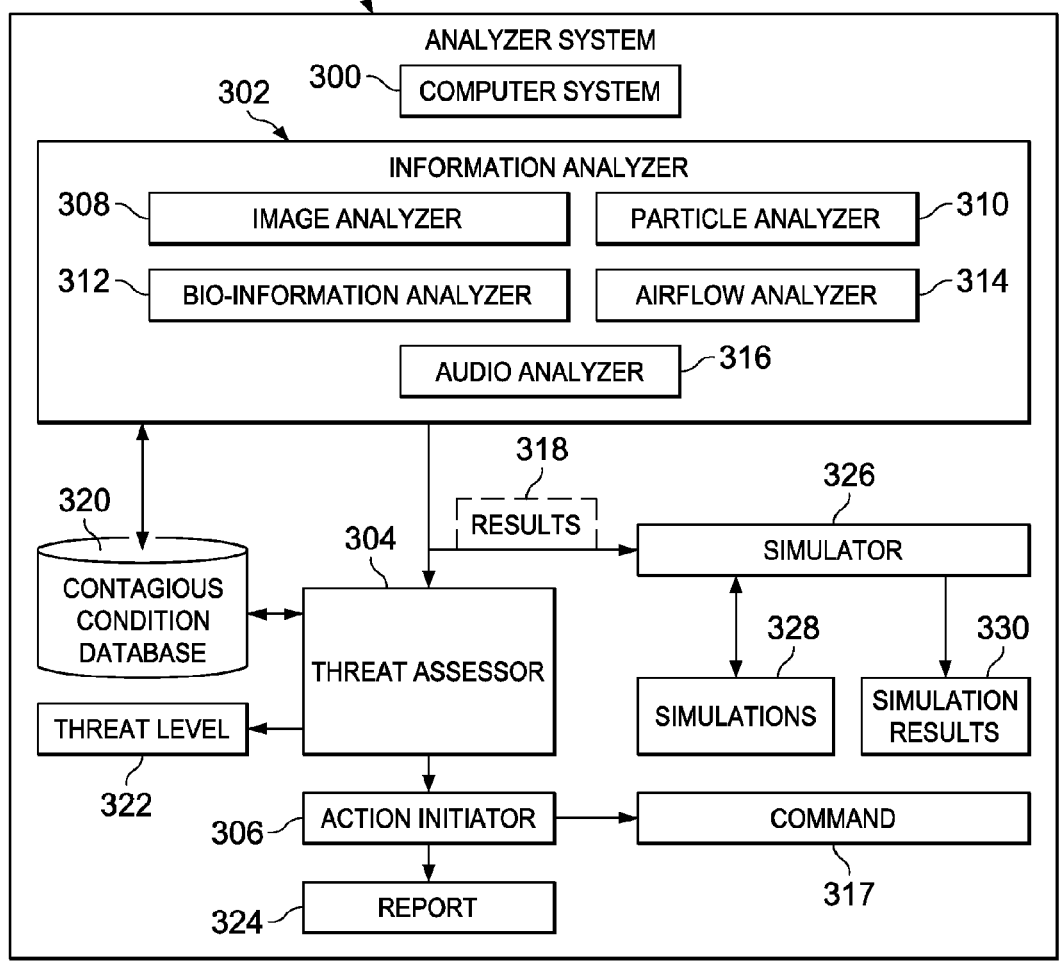

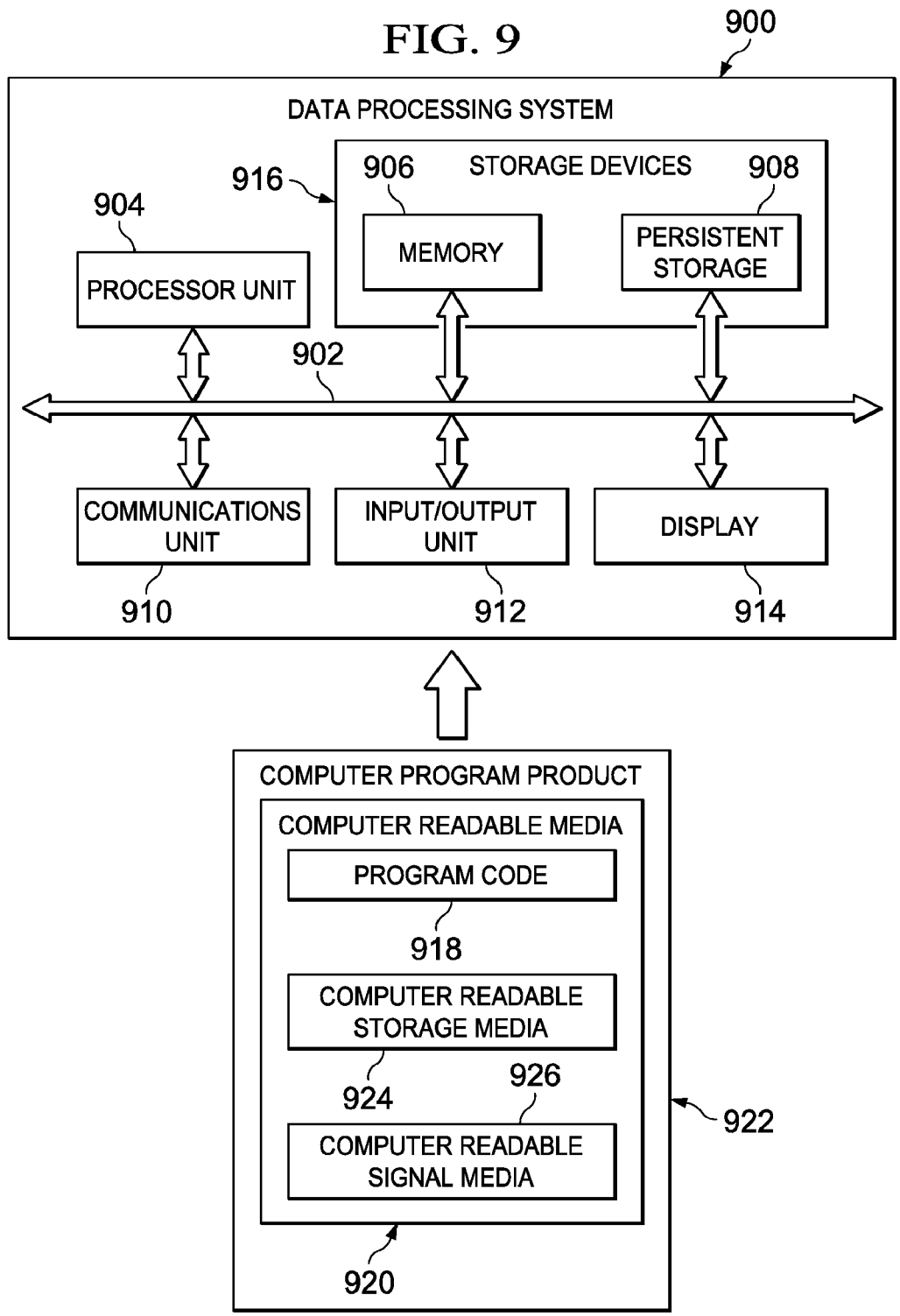

INFECTIOUS DISEASE DETECTION SYSTEM

This Application is a divisional of U.S. patent application Ser. No. 13/302,245, filed Nov. 22, 2011, status allowed, the contacts of which application is incorporated herein by reference in its entirety.

BACKGROUND INFORMATION

1. Field

The present disclosure relates generally to passenger areas and, in particular, to detection and reduction of contagious conditions in passenger areas.

2. Background

Infectious diseases may be transmitted by passengers during travel. Currently, over one billion passengers travel by air annually. With the growing mobility of people and the popularity of air travel, the potential for transmission of diseases between passengers before, during, and after flights has increased. Infectious contagious diseases may be transmitted from infected passengers to healthy passengers during air travel. These infections may arise naturally, in epidemics, or by other means. The prevalence of air travel between the continents has increased the potential spread of these infections from local "hot spots" more quickly than before.

One manner in which the transmission of infectious diseases may be decreased is through managing the filters and the recirculation of air in the aircraft. Infectious diseases may be transmitted through inhalation and/or skin contact with airborne particulates, by direct physical contact between people or objects, and other mechanisms. With the use of filters and increased introduction of fresh air, the transmission of infectious diseases within a passenger cabin may be reduced.

In addition, face masks are personal means for reducing the transmission of airborne particulates that also may be used to reduce the transmission of infectious diseases. Passengers may wear masks at the airport as well as on the aircraft to filter the air being exchanged between people and the environment.

Although these mechanisms may be used to reduce the transmission of infectious diseases; costs, personnel issues, and social issues are present.

Therefore, it would be desirable to have a method and apparatus that takes into account at least some of the issues discussed above as well as possibly other issues.

SUMMARY

In one illustrative embodiment, a method for managing a zone is provided. Information is obtained about an environment in the zone with a sensor system. A determination is made by an analyzer system as to whether a contagious condition is present in the zone using the information from the sensor system. An action is performed by a management system in response to the contagious condition being present.

In another illustrative embodiment, similar to that stated above, an apparatus for managing contagious conditions comprises a sensor system, an analyzer system, and a management system. The sensor system is configured to obtain information about an environment in a zone with a sensor system. The analyzer system is configured to determine whether a contagious condition is present in the zone using the information. The management system is configured to perform an action in response to the contagious condition being present.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and advantages thereof will best be understood by reference to the following detailed description of an illustrative embodiment of the present disclosure when read in conjunction with the accompanying drawings, wherein:

FIG. 3 is an illustration of a block diagram of an analyzer system in accordance with an illustrative embodiment;

FIG. 9 is an illustration of a data processing system in accordance with an illustrative embodiment.

DETAILED DESCRIPTION

The different illustrative embodiments recognize and take into account one or more considerations. For example, they recognize and take into account that although filters and the introduction of fresh air in the passenger cabins of an aircraft may reduce the transmission of contagions, other locations are present in which the transmission of contagions may occur. For example, they recognize and take into account that contagions also may be transmitted in other passenger areas in an airport or other places that people may congregate for a period of time. Further, although the use of face masks may reduce the emission and inhalation of ventilation of airborne contagions, these face masks are not effective against pathogens that are transmitted by direct contact. This direct contact may occur with doorknobs, handles, clothing, hair, and other fomites.

The different illustrative embodiments recognize and take into account that passenger areas are locations where contagions may be spread. Further, these areas are also areas in which the spread of contagions may be managed. It is recognized and taken into account that passenger areas, such as waiting areas, boarding lounges, and walkways, are areas in which passengers may spend time prior to boarding or after exiting an aircraft.

Currently available solutions do not take into account boarding processes, such as those for commercial air flights. Passengers may spend several minutes walking slowly or waiting in a covered walkway while moving towards the entrance to a vehicle, such as an aircraft. The different examples illustrated recognize and take into account that monitoring these and other areas may be used to reduce the spread of infectious diseases.

With the amount of time spent by passengers in these areas, mechanisms may be used to determine whether contagions may be present in the areas, and actions may be taken to reduce the spread of these contagions. As a result, it would be desirable to have a method that aids in detecting the presence of people who may be infected and can potentially become transmitters of infectious diseases.

Thus, the illustrative embodiments provide a method and apparatus for managing a zone in which people may be located. Information about people in the zone is obtained using a sensor system. A determination is made as to whether a contagious condition is present in the zone using this information. An action may be performed in response to the contagious condition being present.

Figure 1:
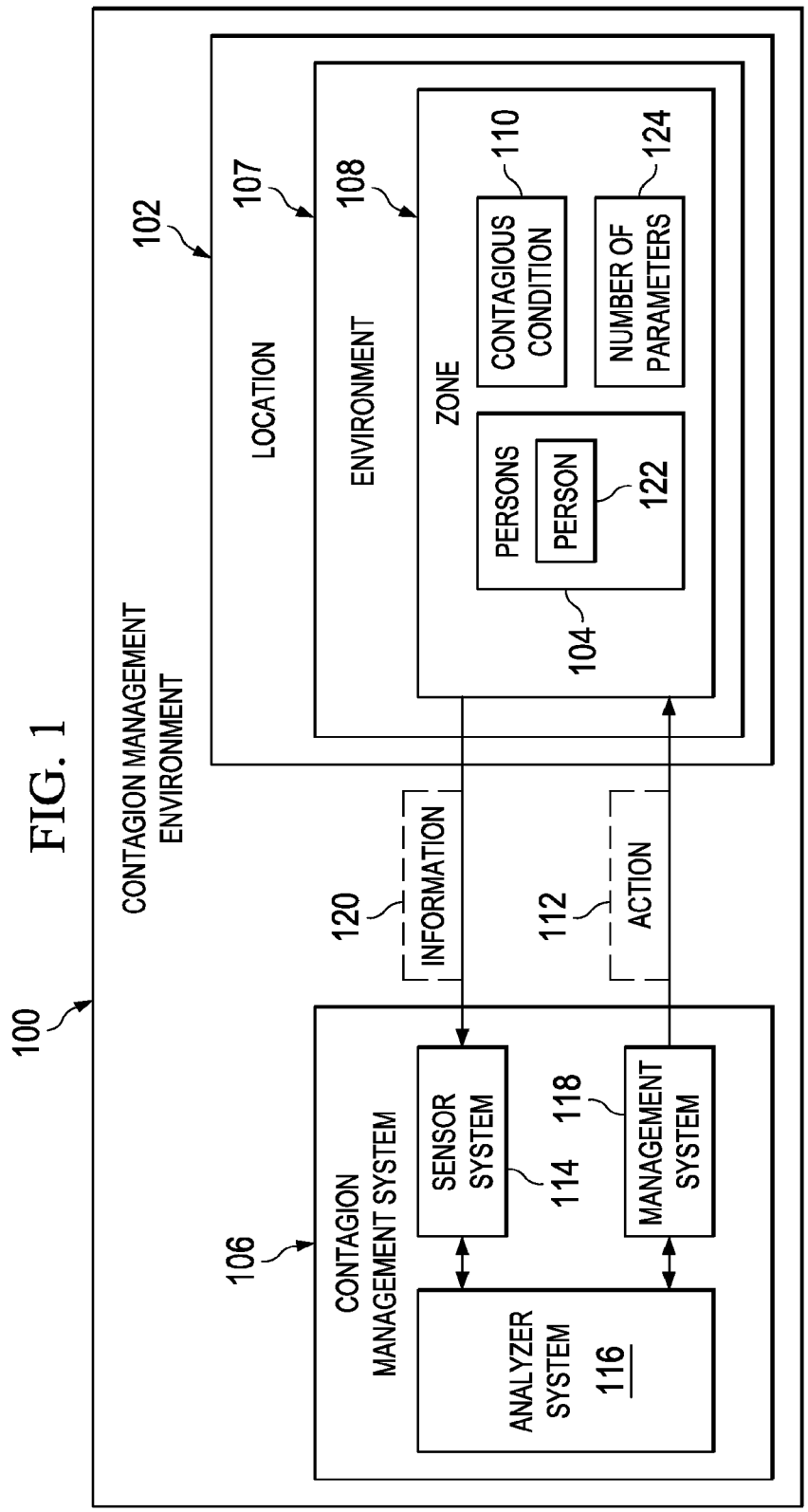
FIG. 1 is an illustration of a block diagram of a contagion management environment in accordance with an illustrative embodiment.

With reference now to the figures and, in particular, with reference to FIG. 1, an illustration of a block diagram of a contagion management environment is depicted in accordance with an illustrative embodiment. In this illustrative example, contagion management environment 100 includes location 102 in which persons 104 may be located. Location 102 may be, for example, without limitation, an airport, a train station, a bus station, a mall, a stadium, an office building, and other suitable types of locations in which contagion management may be desired.

As depicted, contagion management may be performed for location 102 using contagion management system 106 that may manage environment 107 in zone 108 located in location 102. In these illustrative examples, contagion management system 106 may determine whether contagious condition 110 is present and initiate action 112 if contagious condition 110 is detected. In these illustrative examples, these different operations may be performed in real-time. In other words, the determination of whether contagious condition 110 is present and the initiation of action 112 may be performed as quickly as possible by contagion management system 106 without an intentional delay.

In these illustrative examples, contagious condition 110 is a situation in which action 112 may be needed. For example, contagious condition 110 may mean that a person or persons 104 may have symptoms indicating the presence of an infectious disease. In this example, contagious condition 110 may be verified. In another example, contagious condition 110 may be a situation in which a contagion for an infectious disease has been identified as being present in zone 108. In other words, contagious condition 110 may or may not be present.

In this illustrative example, contagion management system 106 comprises sensor system 114, analyzer system 116, and management system 118. Sensor system 114, analyzer system 116, and management system 118 are implemented using hardware and also may include software.

Sensor system 114 is configured to collect information 120 about zone 108. Sensor system 114 may comprise sensors selected from one of an audio sensor, a video camera, an infrared sensor, an air analysis system, and other suitable types of sensors. In particular, sensor system 114 collects information 120 about environment 107 in zone 108. For example, sensor system 114 may collect information 120 about the condition of persons 104 in zone 108 as well as about conditions for environment 107 in zone 108. These other conditions may include, for example, a presence of bacteria, pollen, viruses, and/or other particulates that may be present on surfaces or in the air in environment 107 within zone 108.

Analyzer system 116 uses information 120 to determine whether contagious condition 110 is present and to identify action 112 if contagious condition 110 is present in zone 108.

For example, analyzer system 116 may determine whether contagious condition 110 originated with person 122 in persons 104. If person 122 is identified as originating contagious condition 110, then action 112 may be taken to reduce contagious condition 110.

In these illustrative examples, contagious condition 110 is an infectious disease. Analyzer system 116 also may be configured to identify specific contagious conditions. For example, analyzer system 116 may be configured to identify particular strains of the flu, the Ebola virus, tuberculosis, hemorrhagic fever, and/or any other contagion that can be transmitted from one person to another. In another illustrative example, analyzer system 116 may be configured to identify generalized symptoms of common infectious diseases without identifying a particular strain. For example, the presence of an elevated body temperature, coughing, sweating, and other symptoms may indicate the presence of an infectious disease.

As depicted, management system 118 is a hardware system and may include software. Management system 118 may change number of parameters 124 in zone 108. A number, as used herein with reference to items, means one or more items. For example, number of parameters 124 is one or more parameters. Number of parameters 124 may be any parameters that are selected to reduce contagious condition 110. For example, a parameter in number of parameter 124 may be a direction of airflow, a type of light, a temperature, passenger movement, humidity, and other suitable parameters.

In these illustrative examples, zone 108 may be selected as an area in location 102 in which the location of persons 104, the movement of persons 104, or a combination of the two is such that sensor system 114 is able to collect information 120 in a manner that allows analyzer system 116 to determine whether contagious condition 110 is present. Further, zone 108 also may be selected as an area in location 102 that allows for action 112 to be taken. This action may be, for example, changing number of parameters 124 in a manner that reduces contagious condition 110.

In these illustrative examples, zone 108 may be selected from one of a corridor, a lounge, a restroom, a gate waiting area, a walkway, a passenger boarding bridge, an eating area, a security screening area, a check-in area, a baggage area, a passenger area, and other suitable locations.

Thus, with the use of contagion management system 106, a risk of contagious conditions may be reduced. In particular, a risk of disease transmission may be reduced through the use of contagion management system 106.

In these illustrative examples, contagion management system 106 may be permanently or temporarily set up in location 102 about environment 107 in zone 108. For example, sensor system 114 may be set up in different locations during different times of the year or in response to different alerts about contagious conditions that may occur. For example, sensor system 114 may be set up during flu season or in response to an outbreak of a particular type of infectious disease.

Figure 2:
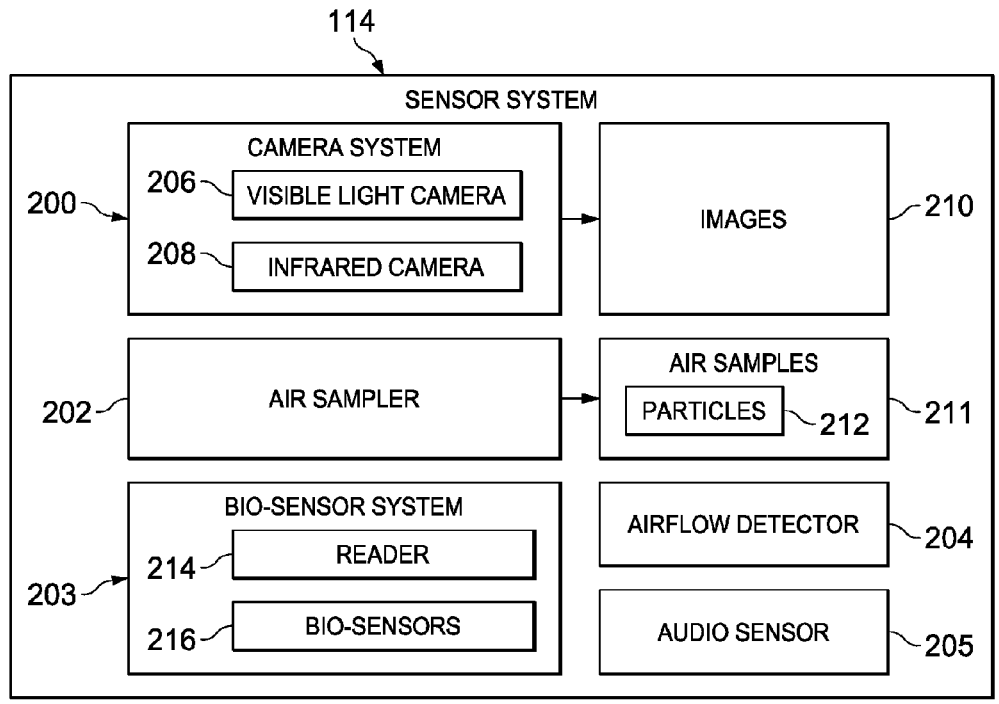
FIG. 2 is an illustration of a block diagram of a sensor system in accordance with an illustrative embodiment.

With reference next to FIG. 2, an illustration of a block diagram of a sensor system is depicted in accordance with an illustrative embodiment. In this illustrative example, sensor system 114 may include at least one of camera system 200, air sampler 202, bio-sensor system 203, airflow detector 204, audio sensor 205, as well as other components.

As used herein, the phrase "at least one of", when used with a list of items, means different combinations of one or more of the listed items may be used and only one of each item in the list may be needed. For example, "at least one of item A, item B, and item C" may include, for example, without limitation, item A or item A and item B. This example also may include item A, item B, and item C, or item B and item C. In other examples, "at least one of" may be, for example, without limitation, two of item A, one of item B, and 10 of item C; four of item B and seven of item C; and other suitable combinations.

In other words, different types of sensors are illustrated in FIG. 2 for sensor system 114. Multiple sensors of the same type may be used in implementing sensor system 114.

In this illustrative example, camera system 200 may include at least one of visible light camera 206, infrared camera 208, and other suitable types of cameras. Visible light camera 206 is configured to generate images 210. Images 210 may be still images or may be sequential images for a video.

Images 210 are used to identify actions of persons 104 in FIG. 1, movement of persons 104, or both. For example, visible light camera 206 may be configured to generate images 210 of a person sneezing or coughing. Infrared camera 208 is configured to generate images 210 from which information about persons 104, such as body temperature, can be identified at different locations on the body of a person in persons 104.

Air sampler 202 is configured to collect air samples 211 from environment 107 in zone 108 in FIG. 1. Air samples 211 may contain particles 212. Particles 212 may be analyzed to identify whether contagions are present and what type of contagions may be present in particles 212.

Bio-sensor system 203 may include reader 214 and bio-sensors 216. Bio-sensors 216 may be associated with one or more of persons 104 in zone 108. For example, bio-sensors 216 may be on boarding passes carried by passengers in persons 104. In other examples, bio-sensors 216 may be worn on the clothing of persons 104. Bio-sensors 216 may generate an indication of a particular condition.

Additionally, bio-sensors 216 may be associated with other objects in zone 108 at location 102 in FIG. 1. For example, bio-sensors 216 may be placed in locations in zone 108 where fomites might be present. These fomites may be, for example, without limitation, surfaces touched by people or other areas through which people may travel. These surfaces may be, for example, handrails, doorknobs, and other surfaces that may be considered a fomite. Bio-sensors 216 may be placed on or near these surfaces.

In this illustrative example, a bio-sensor in bio-sensors 216 may include a biological element, a transducer, and a processor. The biological element may be, for example, a biological material that is sensitive to a particular contagion or set of contagions. For example, a biological element may react with the DNA from a contagious bacteria or with the RNA from a flu virus.

The transducer may generate a signal in response to a reaction of the biological element with the contagion. The signal processor may display or send an indication of a presence of a contagion over a wireless communications link. This indication may be read by reader 214 in bio-sensor system 203.

This indication may be a wireless signal transmitted to reader 214 in bio-sensor system 203 when reader 214 is remote to bio-sensors 216. In other illustrative examples, the indication may be displayed on a bio-sensor in bio-sensors 216. For example, visible light camera 206 may generate images 210 of a bio-sensor on a boarding pass of a person or persons 104 that may be carrying contagions that pose contagious condition 110.

In another illustrative example, the transducer and processor may not be present. For example, bio-sensors 216 may be configured to change a particular feature, such as color, when in contact with a particular contagion, making the change in bio-sensors 216 visually identifiable in images generated by visible light camera 206.

In yet another illustrative example, sensor system 114 also may include airflow detector 204. Airflow detector 204 may provide information about airflow in zone 108.

Audio sensor 205 is configured to detect sounds of persons 104 in zone 108. These sounds may include, for example, sounds of a person sneezing, coughing, or some other suitable sound that may indicate a presence of a contagion being spread.

Turning now to FIG. 3, an illustration of a block diagram of an analyzer system is depicted in accordance with an illustrative embodiment. In this illustrative example, some or all of analyzer system 116 may be implemented using computer system 300.

Computer system 300 is a number of computers. When more than one computer is present in computer system 300, those computers may be in communication with each other. The communication may be provided using a wireless communications link, a network, a shared memory, or some other suitable communication mechanism. In these illustrative examples, analyzer system 116 may include information analyzer 302, threat assessor 304, and action initiator 306.

Information analyzer 302 may include hardware, software, or a combination of the two. Parts of information analyzer 302 may be implemented using computer system 300, while other parts of information analyzer 302 may be implemented using other hardware devices.

For example, image analyzer 308 in information analyzer 302 may use images 210 in FIG. 2 in information 120 in FIG. 1 generated by visible light camera 206 to determine whether contagious condition 110 is present.

More specifically, image analyzer 308 may use images 210 to identify information about persons 104 in FIG. 1. For example, image analyzer 308 may determine whether a person or persons 104 in zone 108 has coughed, sneezed, or performed some other action that may indicate contagious condition 110. As yet another example, image analyzer 308 may identify whether blood is present when a person in persons 104 coughs or sneezes. In still another example, image analyzer 308 may determine if a person is sweating.

Further, images 210 may include bio-sensors 216 in FIG. 2 worn by persons 104. The images of bio-sensors 216 may be used to determine whether a particular contagion is present when bio-sensors 216 generate visual indications for the particular contagion. For example, bio-sensors 216 may be configured to turn red when in contact with a particular contagion. Images 210 may be used by image analyzer 308 to identify the presence of this contagion on a boarding pass or other item carried by a person in persons 104.

Images 210 generated by infrared camera 208 in FIG. 2 may be used by image analyzer 308 to generate additional information about persons 104. For example, image analyzer 308 may generate a temperature profile for part or all of a person. Additionally, images 210 also may be analyzed by image analyzer 308 to identify body fluid ejection patterns when a person sneezes or coughs.

Information analyzer 302 also may include particle analyzer 310. Information analyzer 302 may perform an analysis of particles 212 in FIG. 2 to generate information about particles 212.

Particle analyzer 310 may identify particles 212 obtained by air sampler 202 in FIG. 2. Particle analyzer 310 may be configured to detect potential contagions in zone 108 from particles 212 collected in air samples 211 by air sampler 202 in FIG. 2. Particle analyzer 310 may be configured to indicate the presence of a particular type of contagion. Further, particle analyzer 310 may be configured to indicate when the level of a particular contagion within zone 108 has reached a desired threshold that may make zone 108 particularly susceptible to the transmittal of infectious disease between persons 104. This level may be measured in parts per unit of air.

Further, if deoxyribonucleic acid (DNA) is present in particles 212, the DNA may be amplified using various techniques to provide an amount of DNA needed to identify a particle in particles 212. This amplification of DNA may be performed using various techniques, such as polymerase chain reaction (PCR) processes and/or other suitable processes.

In these illustrative examples, real-time polymerase chain reaction processes may be used to identify particles within a desired time. In another example, kinetic polymerase chain reaction processes also may be used. These processes may detect DNA as the polymerase chain reaction process occurs rather than detecting the DNA at the end of the process. For example, particle analyzer 310 may be implemented using a BioLaz™ Real-Time Microbial Monitor, which is available from Particle Measuring Systems, Inc. The particles identified using this technique may be, for example, viruses, bacteria, fungus, organic allergens, and other particles that may have DNA.

Bio-information analyzer 312 is configured to analyze information from bio-sensor system 203 in FIG. 2. Bio-information analyzer 312 may indicate a presence of a contagion.

Airflow analyzer 314 is configured to obtain information from airflow detector 204 in FIG. 2. Airflow analyzer 314 may identify airflow patterns in zone 108.

Audio analyzer 316 is configured to identify information received from audio sensor 205 in FIG. 2. Audio analyzer 316 may identify body fluid ejection patterns. Audio analyzer 316 may identify these patterns in conjunction with image analyzer 308 in these depicted examples.

In these illustrative examples, the information identified about persons 104 from images 210, airflow patterns, and the information about particles 212 forms results 318. Results 318 are sent to threat assessor 304.

Threat assessor 304 uses results 318 to determine whether contagious condition 110 is present. In particular, threat assessor 304 may analyze results 318 using contagious condition database 320 to determine whether contagious condition 110 is present.

For example, contagious condition database 320 also may include identifications of contagious conditions based on actions, temperatures, and other information gathered about persons 104 in zone 108. This information about persons 104 may be used to identify symptoms of a contagious disease. For example, an identification of a high fever, excessive sweating, and other symptoms may indicate that a person in persons 104 has an infectious disease.

Also, contagious condition database 320 may include identifications of contagious conditions based on the identification of particles 212. The identification of particles 212 may indicate a presence of a contagion for an infectious disease.

If contagious condition 110 is present, threat assessor 304 may identify a severity of contagious condition 110. In one illustrative example, threat assessor 304 generates threat level 322. Threat level 322 may indicate that contagious condition 110 is absent or may indicate a level of severity of contagious condition 110. Threat level 322 may then be used by action initiator 306 to identify action 112 to be performed.

The airflow and body fluid ejection patterns may be used by threat assessor 304 to identify the projected spread of contagions in zone 108. In these illustrative examples, the projected spread may be a factor in identifying threat level 322.

Also, threat assessor 304 may identity a source originating contagious condition 110. The source may be identified from results 318 generated by information analyzer 302. In these illustrative examples, the source in zone 108 may be at least one of a floor surface, an object dropped by a person, a fomite, a person, a hand rail, a doorknob, and other sources.

As depicted, action initiator 306 uses threat level 322 to initiate action 112 in FIG. 1. As described above, action 112 may include changing number of parameters 124, generating alerts, sending reports, and other suitable types of actions for action 112. Action 112 may be identified using contagious condition database 320. Contagious condition database 320 may include actions that may be taken in response to a determination that contagious condition 110 is present.

In these illustrative examples, action initiator 306 may send command 317 to management system 118 in FIG. 1 to change or initiate action 112. In this example, action 112 changes number of parameters 124 in zone 108. The airflow pattern within zone 108 may be a factor in which parameters and the extent to which values for number of parameters 124 may be changed.

Additionally, action initiator 306 also may identify one or more persons in persons 104 suspected of carrying an infectious disease. These persons may be identified as having contagious condition 110. Action 112 may be to separate these persons from other persons in persons 104 and indicate that an additional examination should be performed. Performing the additional examination may determine whether these persons actually carry an infectious disease. For example, action 112 may be to send an instruction to the passengers identified as having contagious condition 110 to move to another area. In another example, employees or other operators may be instructed to escort the persons identified to another area for an additional examination.

In yet another illustrative example, action 112 may include initiating cleaning of zone 108, more frequent cleaning of zone 108, use of different cleaning agents in zone 108, and other suitable actions. In still another illustrative example, action 112 may include closing off zone 108 to people until environment 107 is considered to no longer have contagious condition 110.

In still other illustrative examples, action 112 may be to perform an additional examination of the source of contagious condition 110. This examination may involve taking samples from the source, collecting the source, or other suitable actions to examine the source.

For example, contagious condition 110 may be identified, but the actual nature of contagious condition 110 may not be known. In one example, a tissue dropped on the ground after a person sneezes in the tissue may be identified as contagious condition 110. However, whether bacteria, a virus, or some other contaminant is present is unknown. An additional examination of this source may be made.

Action initiator 306 also may generate report 324. Report 324 may include information about contagious condition 110. Additionally, report 324 also may include an identification of actions that should be taken. Report 324 may be stored or sent to an airline, airport management, a government agency, or some other suitable destination. These reports may result in other actions being initiated.

Additionally, analyzer system 116 also may include simulator 326. Simulator 326 may use results 318 in simulations 328 of zone 108. Simulation results 330 from simulations 328 may be used to identify changes to zone 108 to identify optimal parameters for number of parameters 124 in zone 108.

For example, changes to airflow, lighting, temperature, and other parameters in zone 108 may be made. These changes to number of parameters 124 are changes that may be made without detecting contagious condition 110. Instead, these changes may be made to reduce the spread of contagious condition 110 if contagious condition 110 is detected in zone 108. For example, the airflow may be changed such that the airflow is configured to move in a direction selected from one of towards a ceiling in zone 108 and towards a flow in zone 108. The direction selected may depend on the airflow system used in zone 108.

Simulator 326 may also be used to simulate the potential radius of infection once contagious condition 110 has been identified. Simulation results 330 from simulations 328 may be used, for example, to determine the most likely location for the spread of infectious disease, the most effective route to redirect persons 104 away from the area, and what number of parameters 124 in other areas of the airport needs to be altered to neutralize contagious condition 110.

For example, simulation results 330 from performing simulations 328 may be used to perform upgrades to ventilation systems in zone 108. As another example, simulation results 330 also may be used to change procedures for moving through zone 108. For example, walking pace and walking patterns may be identified that reduce the possibility of a contagion being passed from one person to another person in zone 108. These are changes to number of parameters 124 in addition to changes to number of parameters 124 made in response to detecting contagious condition 110.

The actual action taken may depend on the components present in management system 118 and the configuration of zone 108. The actions illustrated in the different depicted examples are only meant to provide illustrative examples of action 112 and are not meant to be limiting to the manner in which action 112 may be implemented.

Depending on the modularity of components in contagion management system 106 in FIG. 1, a variety of different actions may be selected or implemented. For example, different types of sensors may be added or used in sensor system 114. Further, analyzer system 116 may be configured to add or use different types of analysis systems to identify a contagious condition.

In addition, different components may be used in management system 118 to perform actions. The actions that may be selected may be based on the components used in management system 118. In these illustrative examples, components for these different systems may be added or exchanged, depending on the particular implementation. The change of components may be selected based on the contagious condition that may be present. In other words, if a different contagious condition is predicted to be present, components in contagion management system 106 may be changed to target the particular contagious condition.

Figure 4:
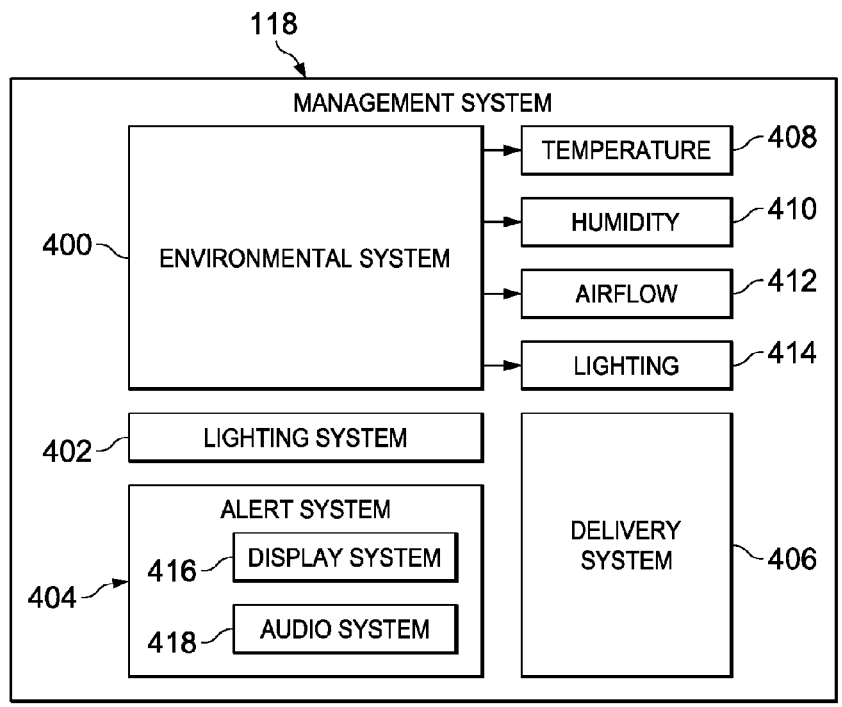
FIG. 4 is an illustration of a block diagram of a management system in accordance with an illustrative embodiment.

Turning next to FIG. 4, an illustration of a block diagram of a management system is depicted in accordance with an illustrative embodiment. In this illustrative example, management system 118 may include environmental system 400, lighting system 402, alert system 404, and delivery system 406, as well as other types of systems, depending on the particular implementation.

Delivery system 406 may be configured to deliver items in zone 108 to reduce contagious condition 110 in FIG. 1. For example, delivery system 406 may make anti-bacterial liquids, masks, and other items available to persons 104 in zone 108.

Management system 118 may perform action 112 in FIG. 1 in response to receiving command 317 from action initiator 306 in analyzer system 116 in FIG. 3. In particular, command 317 may be received from action initiator 306.

Environmental system 400 may be used to change one or more parameters in number of parameters 124 in FIG. 1. For example, environmental system 400 may change at least one of temperature 408, humidity 410, airflow 412, lighting 414, and other suitable parameters. For example, changes in temperature 408 and humidity 410 may be changed to reduce the viability that a contagion may remain contagious, depending on the contagion identified. For example, the temperature may be decreased to neutralize the contagion.

Airflow 412 also may be changed to potentially move contagions away from persons 104 in zone 108. For example, upward airflow may be initiated or increased. In some examples, downward airflow may be initiated or increased.

Temperature 408, humidity 410, or a combination of the two may be changed to reduce the viability of a contagion in zone 108. In this manner, transmission of a contagion may not cause a spread of an infectious disease if the contagion is rendered inert.

Lighting 414 also may be changed in zone 108. For example, ultraviolet light may be introduced in selected locations of persons 104. For example, persons 104 may place clothing, hands, and other articles under an ultraviolet light in zone 108 if contagious condition 110 is detected. This lighting may reduce the ability of a contagion to infect other people if spread into the air or on surfaces in zone 108.

Alert system 404 may include display system 416 and audio system 418. Display system 416 may comprise display devices that visually present instructions or information to persons 104 in zone 108. For example, the instructions may instruct passengers before a certain point to halt movement. Audio system 418 may include a number of speakers. Instructions may be delivered to persons 104 in zone 108 using audio system 418. For example, audio system 418 may instruct passengers via voice commands to halt movement.

Further, if a particular person or number of persons in persons 104 is identified as originating contagious condition 110, at least one of display system 416 and audio system 418 may be used to instruct those people to move to another area for further testing or diagnosis.

In another illustrative example, environmental system 400, lighting system 402, alert system 404, and delivery system 406 may be configured to activate periodically without analyzer system 116 detecting contagious condition 110. For example, during heightened seasons of infectious disease, management system 118 may be configured to adjust number of parameters 124 based on time cycles, temperature fluctuations, or other suitable factors.

The illustration of contagion management environment 100 in FIG. 1, contagion management system 106, and other components in FIGS. 1-4 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

The different components shown in FIG. 5 and FIG. 6 below may be combined with components in FIGS. 1-4, used with components in FIGS. 1-4, or a combination of the two. Additionally, some of the components in FIG. 5 and FIG. 6 may be illustrative examples of how components shown in block form in FIGS. 1-4 can be implemented as physical structures.

Figure 5:
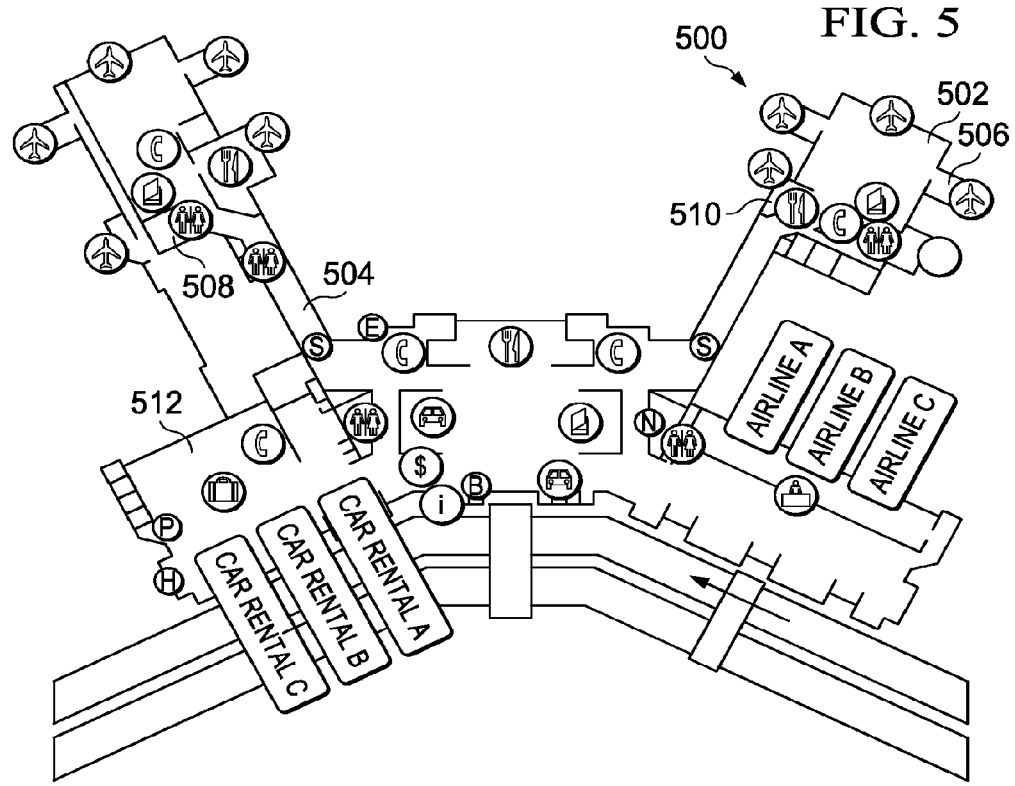
FIG. 5 is an illustration of a location in which a contagion management system may be implemented in accordance with an illustrative embodiment.

With reference next to FIG. 5, an illustration of a location in which a contagion management system may be implemented is depicted in accordance with an illustrative embodiment. In this illustrative example, airport terminal 500 is an example of location 102 in which contagion management system 106 in FIG. 1 may be implemented. Contagion management system 106 may be especially useful in airport terminal 500 to reduce contagious condition 110 in FIG. 1 that may occur in airport terminal 500.

In these illustrative examples, contagion management system 106 may be configured to manage different zones in airport terminal 500. These zones include, for example, without limitation, preboarding lounge 502, concourse 504, passenger boarding bridge 506, restroom 508, eating area 510, and baggage area 512. These areas are examples of areas that may be selected as a zone in which contagion management system 106 manages contagious conditions.

These and other areas may be selected as ones in which the latency of passengers and other people are such that contagious condition 110 may be identified. For example, the latency of passengers or other people in these areas may be one in which the movement of people is slow enough such that contagious condition 110 may be identified and action 112 may be taken. Further, passenger boarding bridge 506 may be especially useful, since passengers may move slowly in the same direction towards a doorway for an aircraft. Passengers may walk slowly or stand in preboarding lounge 502 for periods of time long enough to determine whether contagious condition 110 is present and to take action 112.

Figure 6:
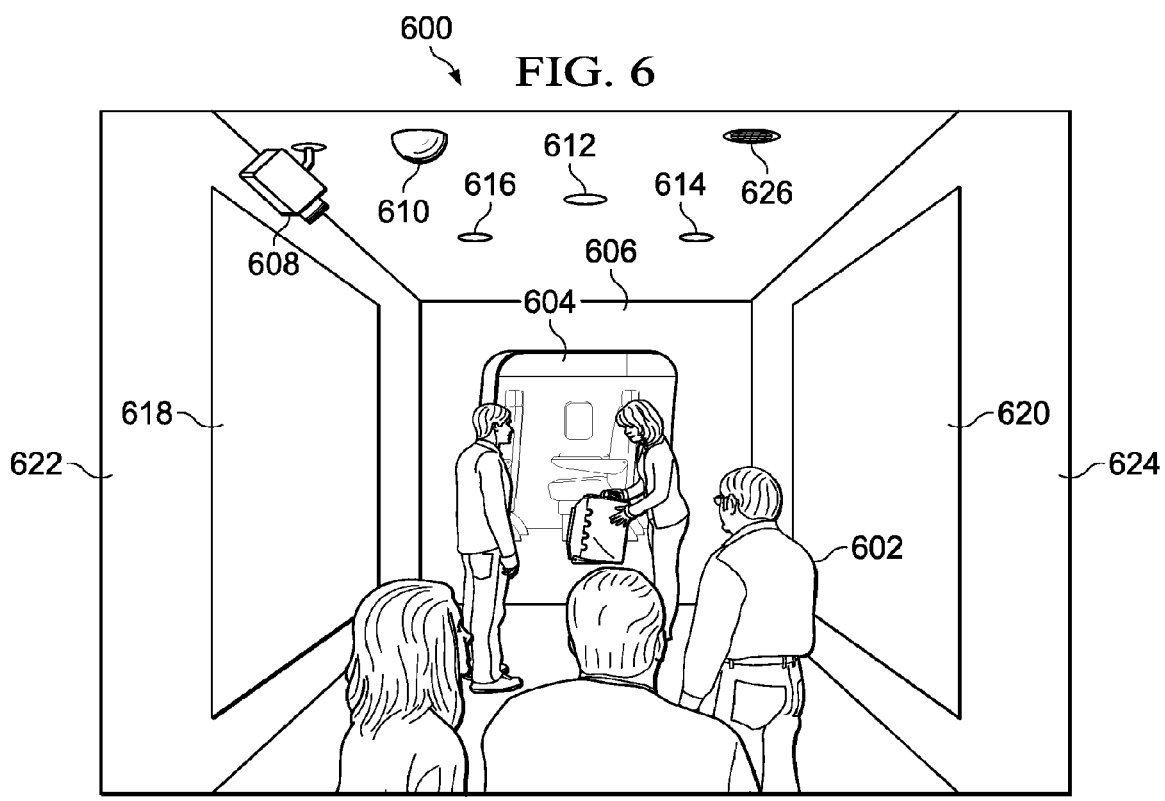
FIG. 6 is an illustration of a passenger boarding bridge in accordance with an illustrative embodiment.

With reference now to FIG. 6, an illustration of a passenger boarding bridge is depicted in accordance with an illustrative embodiment. In this illustrative example, passenger boarding bridge 600 is an example of an area that may be designated as zone 108 for management by contagion management system 106 in FIG. 1. In this illustrative example, passenger boarding bridge 600 is a covered walkway in which passengers 602 may walk towards doorway 604 for aircraft 606.

Sensors, such as visible light camera 608, infrared camera 610, air sampling port 612, air sampling port 614, and microphone 616 may be present. These sensors are examples of sensors that may be used to implement sensor system 114 in FIG. 1. These sensors provide information 120 to analyzer system 116.

Further, display device 618 and display device 620 may be part of alert system 404 in FIG. 4. These display devices are examples of display devices that may be used to implement display system 416 in FIG. 4. Display device 618 and display device 620 are located on wall 622 and wall 624, respectively, in passenger boarding bridge 600. Display device 618 and display device 620 are examples of display devices in display system 416 shown in block form in FIG. 4.

These display devices may display instructions to passengers 602 if contagious condition 110 is detected. These instructions may alter movement of passengers 602 in passenger boarding bridge 600. Further, speaker 626 is an example of a speaker that may be used to implement audio system 418 in FIG. 4. Speaker 626 may provide audibly instructions to passengers 602 in passenger boarding bridge 600.

The illustration of airport terminal 500 in FIG. 5 and passenger boarding bridge 600 in FIG. 6 are not meant to limit the manner in which other illustrative embodiments may be implemented. For example, the different illustrative embodiments may be applied to other locations other than airport terminals. For example, these other locations may include a bus terminal, a subway terminal, a passenger area in a port, and other suitable locations.

The different sensors illustrated in passenger boarding bridge 600 are not meant to limit the type or number of sensors that may be used. For example, a bio-sensor system also may be implemented in passenger boarding bridge 600.

Figure 7:
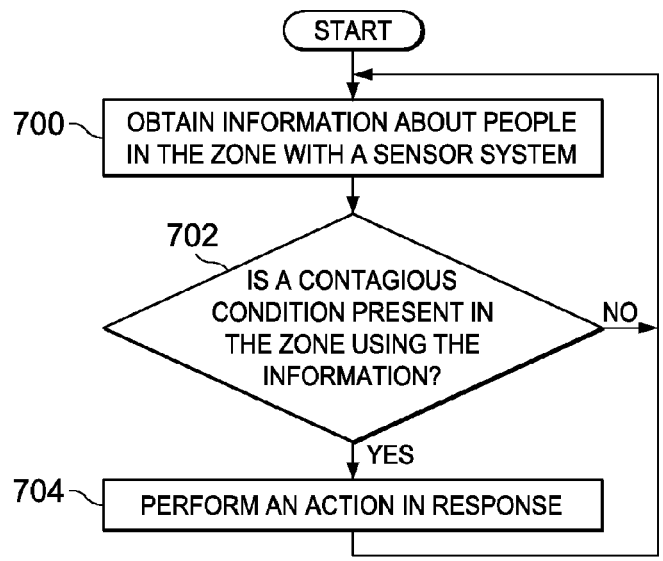
FIG. 7 is an illustration of a flowchart of a process for managing a zone with a contagion management system in accordance with an illustrative embodiment.

With reference now to FIG. 7, an illustration of a flowchart of a process for managing a zone with a contagion management system is depicted in accordance with an illustrative embodiment. This process may be implemented in contagion management system 106 to manage zone 108 in FIG. 1.

The process begins by obtaining information about people in the zone with a sensor system (operation 700). A determination is made as to whether a contagious condition is present in the zone using the information (operation 702). If a contagious condition is not present, the process returns to operation 700.

With reference again to operation 702, if a determination is made that a contagious condition is present in the zone, the process performs an action in response (operation 704), with the process then returning to operation 700.

Figure 8:
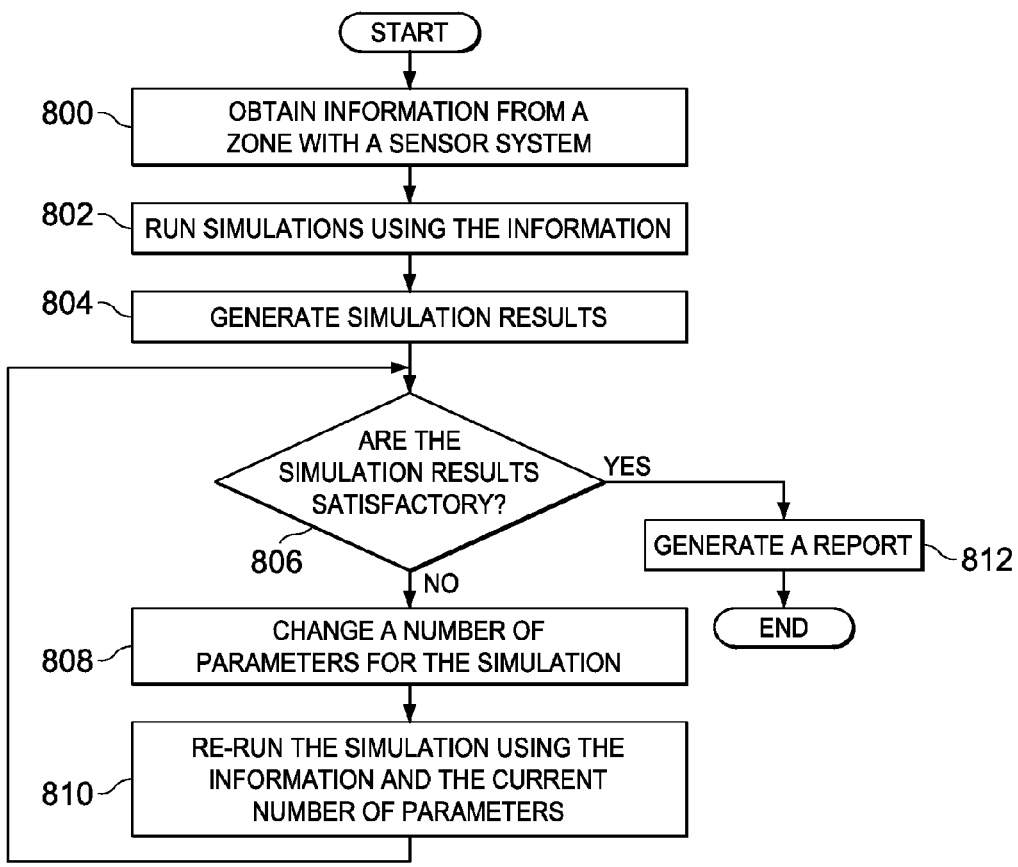
FIG. 8 is an illustration of a flowchart of a process for identifying changes to a zone in accordance with an illustrative embodiment.

With reference now to FIG. 8, an illustration of a flowchart of a process for identifying changes to a zone is depicted in accordance with an illustrative embodiment. The process illustrated in FIG. 8 may be implemented in contagion management system 106 in FIG. 1. In particular, this process may be implemented in simulator 326 in FIG. 3.

The process begins by obtaining information from a zone with a sensor system (operation 800). This information may be obtained over a period of time. For example, the information may be obtained over a period of time that is selected from one of a day, a week, a month, a year, or some other suitable period of time.

The process then runs simulations using the information (operation 802). This simulation may be used to identify whether contagious conditions are present and how they may be spread in the zone being simulated. The process then generates simulation results (operation 804). These results may identify the spreading of contagions that may cause infectious diseases.

A determination is made as to whether the simulation results are satisfactory (operation 806). If the simulation results are not satisfactory, a number of parameters for the simulation are changed (operation 808). The process then re-runs the simulation using the information and the current number of parameters (operation 810). The process then returns to operation 806. If the results are satisfactory, then a report is generated (operation 812), with the process terminating thereafter.

This report may identify changes to the zone being monitored. Further, these changes may include upgrades to environmental systems, air locations, vents, and other suitable types of changes. Further, these simulations also may be used to simulate a zone that is in a design phase. With the simulations, changes may be made in constructing the zone in a manner that reduces contagious conditions.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the block may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Turning now to FIG. 9, an illustration of a data processing system is depicted in accordance with an illustrative embodiment. Data processing system 900 may be used to implement one or more computers in computer system 300 for analyzer system 116 in FIG. 3. In this illustrative example, data processing system 900 includes communications framework 902, which provides communications between processor unit 904, memory 906, persistent storage 908, communications unit 910, input/output (I/O) unit 912, and display 914. In this example, communications framework 902 may take the form of a bus system.

Processor unit 904 serves to execute instructions for software that may be loaded into memory 906. Processor unit 904 may be a number of processors, a multi-processor core, or some other type of processor, depending on the particular implementation.

Memory 906 and persistent storage 908 are examples of storage devices 916. A storage device is any piece of hardware that is capable of storing information, such as, for example, without limitation, data, program code in functional form, and/or other suitable information either on a temporary basis and/or a permanent basis. Storage devices 916 may also be referred to as computer readable storage devices in these illustrative examples. Memory 906, in these examples, may be, for example, a random access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that may be connected to data processing system 900. For example, input/output unit 912 may provide a connection for user input through a keyboard, a mouse, and/or some other suitable input device. Further, input/output unit 912 may send output to a printer. Display 914 provides a mechanism to display information to a user.

Instructions for the operating system, applications, and/or programs may be located in storage devices 916, which are in communication with processor unit 904 through communications framework 902. The processes of the different embodiments may be performed by processor unit 904 using computer-implemented instructions, which may be located in a memory, such as memory 906.

These instructions are referred to as program code, computer usable program code, or computer readable program code that may be read and executed by a processor in processor unit 904. The program code in the different embodiments may be embodied on different physical or computer readable storage media, such as memory 906 or persistent storage 908.

Program code 918 is located in a functional form on computer readable media 920 that is selectively removable and may be loaded onto or transferred to data processing system 900 for execution by processor unit 904. Program code 918 and computer readable media 920 form computer program product 922 in these illustrative examples. In one example, computer readable media 920 may be computer readable storage media 924 or computer readable signal media 926.

In these illustrative examples, computer readable storage media 924 is a physical or tangible storage device used to store program code 918 rather than a medium that propagates or transmits program code 918.

Alternatively, program code 918 may be transferred to data processing system 900 using computer readable signal media 926. Computer readable signal media 926 may be, for example, a propagated data signal containing program code 918. For example, computer readable signal media 926 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 900 are not meant to provide architectural limitations to the manner in which different embodiments may be implemented. The different illustrative embodiments may be implemented in a data processing system including components in addition to and/or in place of those illustrated for data processing system 900. Other components shown in FIG. 9 can be varied from the illustrative examples shown. The different embodiments may be implemented using any hardware device or system capable of running program code 918.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus for managing contagious conditions, the apparatus comprising:
   a sensor system configured to
      obtain information about an environment within a zone with the sensor system, the zone comprising an area in which people are located for a time, the sensor system disposed in a ceiling, wall, or floor of the zone, and in which a physical sample is taken from the zone; and
   an analyzer system comprising a number of processors configured to:

analyze at least an air sample to obtain one or more of bio-information, particle information, and airflow pattern information;

determine whether a contagious condition is present in the zone using the information from the sensor system; and identify an action to be performed in response to the contagious condition being present.

2. The apparatus of claim 1, wherein the action comprises changing a parameter in the environment that reduces the contagious condition.

3. The apparatus of claim 2, wherein the parameter is for the zone and is selected from one of a direction of airflow, a type of light, a temperature, passenger movement, and a humidity.

4. The apparatus of claim 1, wherein the action comprises identifying a source originating the contagious condition and indicating an additional examination of the source should be performed.

5. The apparatus of claim 1, wherein the action comprises causing airflow that is configured to move particles away from a person in the zone.

6. The apparatus of claim 5, wherein the action further comprises collecting the particles from the airflow and determining whether a contagion is present in the particles.

7. The apparatus of claim 1, wherein the action comprises presenting an instruction to change a pattern of movement by people in the zone.

8. The apparatus of claim 1, wherein the zone is selected from one of a corridor, a lounge, a restroom, a gate waiting area, a walkway, a security screening area, a baggage area, a passenger boarding bridge, an eating area, a check-in area, and a passenger area.

9. The apparatus of claim 1, wherein the zone comprises a passenger boarding bridge and the sensor system is positioned in part in a ceiling of the passenger boarding bridge.

10. The apparatus of claim 1, wherein the zone comprises, a passenger lounge and the sensor system is positioned at least in part in a ceiling, wall, or floor of the passenger lounge.

11. The apparatus of claim 1, wherein the zone comprises a gate waiting area and the sensor system is positioned at least in part in a ceiling, wall, or floor of the gate waiting area.

12. The apparatus of claim 1, wherein the zone comprises a corridor or a walkway and the sensor system is positioned at least in part in a ceiling, wall, or floor of the corridor or walkway.

13. The apparatus of claim 9, wherein the sensor system is positioned in part in a ceiling of the passenger boarding bridge to draw the at least an air sample from the passenger boarding bridge.

14. The apparatus of claim 13,
wherein the number of processors of the analyzer system is further configured to:

send a command to a management system to change a parameter in the environment.

15. The apparatus of claim 1, wherein the zone comprises a preboarding lounge and the sensor system is positioned at least in part in a ceiling, wall, or floor of the preboarding lounge.

16. The apparatus of claim 1, wherein the zone comprises a gate waiting area and the sensor system is positioned at least in part in a ceiling, wall, or floor of the gate waiting area.

17. The apparatus of claim 1, wherein the zone comprises a corridor or a walkway and the sensor system is positioned at least in part in a ceiling, wall, or floor of the corridor or walkway.

18. The apparatus of claim 1, further comprising:
the number of processors of the analyzer system is further configured to:
analyze the air sample to obtain bio-information, particle information, and airflow pattern information;
assess a threat level based on results obtained from the analyzer system;
analyze the information including obtaining bio-information regarding biohazards and obtaining image information;
perform a simulation using the information; and
send a command to a management system to perform the action in response to the contagious condition being present, including at least causing airflow to move particles away from a person in the zone and activating an alert system;
wherein to activate the alert system, the management system is further configured to deliver instruction to persons in the zone using an audio system and to visually present instructions or information to persons in the zone using a display system;
wherein to perform the simulation, the number of processors of the analyzer system is further configured to identify changes to the zone, and the management system is further configured to implement the changes to the zone;
wherein to perform the simulation, the number of processors of the analyzer system is further configured to identify a radius of infection;
wherein to analyze the information, the number of processors of the analyzer system is further configured to use an infrared camera to develop a temperature profile of the person;
wherein to analyze the information, the number of processors of the analyzer system is further configured to analyze images to identify bodily fluid ejection patterns; and
wherein to analyze the information, the number of processors of the analyzer system is further configured to use an image analyzer, a bio-information analyzer, an audio analyzer, and a particle analyzer.

* * * * *